United States Patent [19]

Goodwin, deceased et al.

[11] 4,174,675
[45] Nov. 20, 1979

[54] ANALYTICAL INSTRUMENT

[76] Inventors: Earl L. Goodwin, deceased, late of Albany, N.Y., by Bette-Lou T. H. Goodwin, executrix, 11 S. Lake Ave., Albany, N.Y. 12208

[21] Appl. No.: 922,329

[22] Filed: Jul. 6, 1978

[51] Int. Cl.² .................................................. G01D 13/22
[52] U.S. Cl. ..................................... 116/323; 33/1 C; 73/23.1
[58] Field of Search .................. 73/23.1; 33/1 C, 1 S, 33/1 BB, 41 B, 174 G, 174 PA; 116/281, 283, 321, 323, 325

[56] References Cited

U.S. PATENT DOCUMENTS

| 1,880,089 | 9/1932 | Heidecorn et al. | 116/323 |
| 3,686,764 | 8/1972 | Oesterritter | 33/1 C |
| 3,862,615 | 1/1975 | Liou | 116/323 |

Primary Examiner—Stephen A. Kreitman

[57] ABSTRACT

The object of the invention is to provide an analytical instrument (25) for use with profile diagrams (1) of materials to monitor and determine whether the detection systems producing such profile diagrams (1) are functioning properly, and to quickly pin-point and identify, among known materials exhibited by such profile diagrams (1), unknown materials exhibited by such profile diagrams (1).

Said analytical instrument (25) has a flat, rectangular-shaped body (29) with three horizontal and parallel slots (61), (63) and (65) formed therethrough and markers (43) of different colors that are adjustably disposed relative to such slots (61), (63) and (65) and secured therewith. Such markers (43) are adjustably disposed respecting a profile diagram (1) to pin-point the materials profiled by such profile diagram (1) with the colored markers (43) being used thereby as color-coded reference markers for known materials profiled.

10 Claims, 4 Drawing Figures

4,174,675

ANALYTICAL INSTRUMENT

DESCRIPTION

1. Technical Field

This invention relates to analytical instruments and particularly to analytical instruments for use with profile diagrams of materials to monitor and determine whether the detection systems producing such profile diagrams are functioning properly, and to quickly pinpoint and identify, among known materials exhibited by such profile diagrams, unknown materials exhibited by such profile diagrams.

2. Background Art

Arora, S. K. *Device for the direct reading of Rf values of two dimensional chromatogramms*. In Lab. Pract. volume number 21, issue number 10: page 730, October 1970. This publication discloses a device in the form of a master sheet for the direct reading of Rf values of two dimensional chromatograms, for Rf reading of solvent value.

DISCLOSURE OF INVENTION

In accordance with the present invention, an analytical instrument is provided, but is not countenanced in the prior art, in the form of a flat, rectangular-shaped body having parallel slots each receiving operatively a plurality of markers of different colors. The markers are adjustable in a horizontal direction relative to and coaxial with the longitudinal axes of such parallel slots, and the analytical instrument has the phenomenon of adjustability and disposition of its markers such that any three of the markers constituting its own set can be disposed, each relative to its own slot, in absolutely aligned vertical relationship normal to the longitudinal axes of such parallel slots.

In utilizing the analytical instrument of this invention with respect to profile diagrams, and in particular with reference to gas chromatograms, it should be appreciated that markers of different colors are adjustably disposed in their respective slots to pin-point the discrete peak points of a known sample of components eluted and profiled on a prior chromatogram of a properly functioning gas chromatograph in order that such analytical instrument can be disposed on a new chromatogram inclusively containing such known sample of components to monitor and determine whether such equipment is presently working properly and with such discretely colored markers being used as reference markers for such discretely known components. Such analytical instrument's self-contained phenomenon of such infinite vertical adjustability and disposition of three of such markers normal to such parallel slots permits such analytical instrument to be further utilized to pinpoint the peak points of components profiled on a chromatogram when the peak points of such components are relatively close to one another. Inclusively in such utilization of the analytical instrument of this invention, same can be utilized by means of the pre-setting of such markers and color-coded use of such markers thusly pre-set to pin-point and localize known eluted components to detect in routine monitoring any unknown component or contaminant being eluted and profiled by the chromatograph.

BRIEF DESCRIPTION OF DRAWINGS

The details of the invention will be described in connection with the accompanying drawing, in which.

BEST MODE FOR CARRYING OUT THE INVENTION

Figure 1:
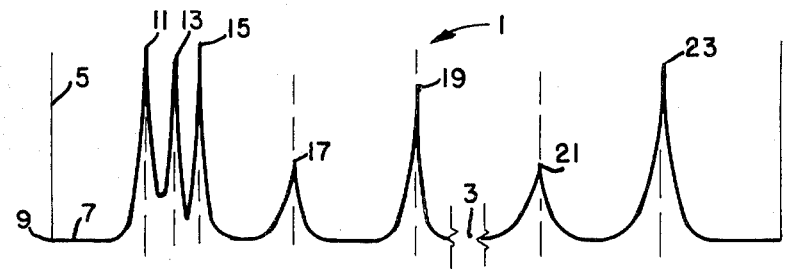
FIG. 1 is a profile diagram of components.

In FIG. 1 of the drawing, reference numeral 1 generally refers to the profile diagram. Profile diagram 1 is shown broken as is indicated by reference numeral 3 applied thereto and signifying that profile diagram 1 is of greater length in a horizontal direction than shown. Such profile diagram 1 represents in particular a gas chromatogram of eluted components depicted in FIG. 1 merely as an arbitrary example to demonstrate and describe therewith utilization of this invention, but without reference to any particular mixture or the accuracy thereof.

Vertical line 5 represents the time zero at which the material is injected into the column of the gas chromatograph. Baseline 7 represents those substantially horizontal portions recorded on such chromatogram when the carrier gas employed in the chromatograph emerges. Viewing line 5 as representing the Y axis, baseline 7 as representing the X axis, the point of intersection 9 of vertical line 5 and baseline 7 as being the origin, the distances X and Y perpendicular to such axes could be considered as being the cartesian or rectangular co-ordinates of the peak points 11, 13, 15, 17, 19, 21 and 23 whose respective abscissae would represent the retention times or elapsed times from the start of the analysis (or the time zero at which the material is injected into the gas chromatograph's column) for the particular components of such injected material to emerge or elute, and, with reference to the respective ordinates of such peak points 11, 13, 15, 17, 19, 21 and 23, the areas under such peak points indicate the concentrations of such particular eluted components.

Each particular component having its own retention time or peak emergence time before such particular component emerges or elutes, this fact leads to the identification of such particular component with such particular and identified component's concentration being determined by the area generated under its peak.

Figure 2:
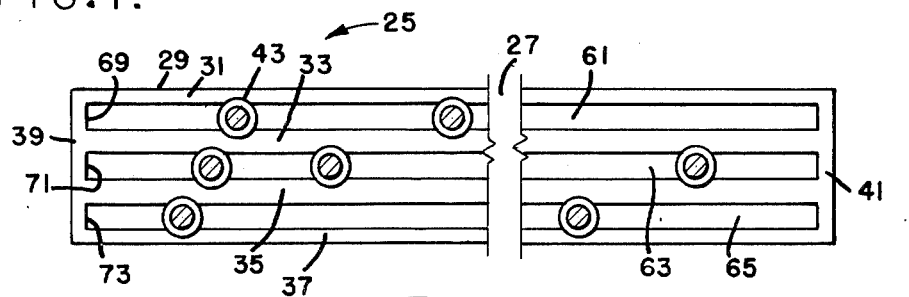
FIG. 2 is a view of the analytical instrument of this invention.
Figure 3:
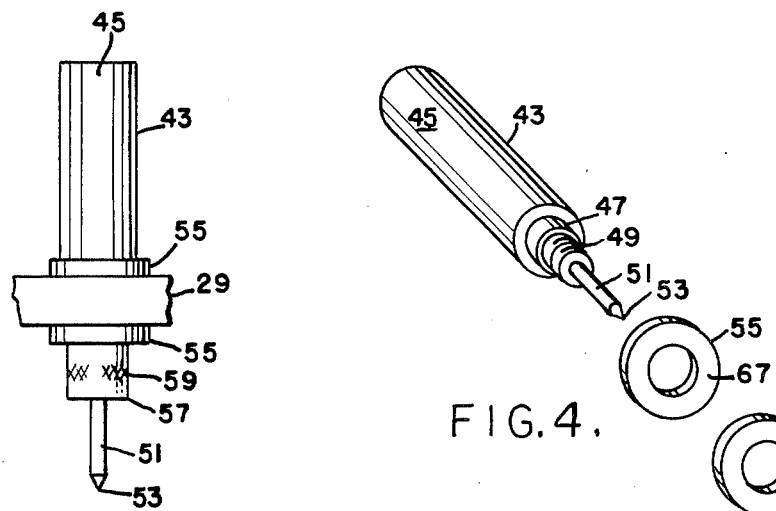
FIG. 3 is a view of a portion of the analytical instrument of this invention.
Figure 4:
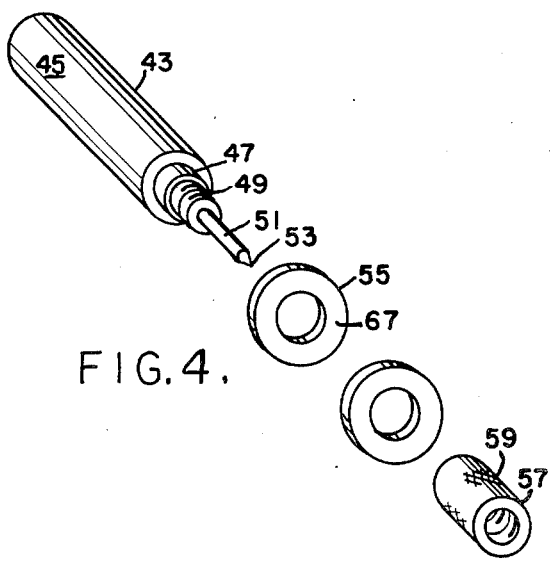
FIG. 4 is an exploded view of the assembly of one of the analytical markers of this invention.

In FIG. 2 of the drawings, reference numeral 25 generally refers to the analytical instrument of this invention that is broken, as indicated by reference numeral 27 applied thereto signifying that instrument 25 is of greater length in a horizontal direction. Analytical instrument 25 comprises a flat, rectangular-shaped body 29 having, as viewed in such FIG. 2, a top horizontal portion 31, two intermediate horizontal portions 33 and 35, a bottom horizontal portion 37, a left vertical side 39 and a right vertical side 41. The horizontal portions 31, 33, 35 and 37 are in parallel relationship with one another and the vertical sides 39 and 41 are in normal relationship to such horizontal portions 31, 33, 35 and 37.

Shown disposed and carried on body 29 are the markers 43, each of which markers 43 comprises an elongated cylindrical body 45 having integral therewith and extending therefrom a reduced cylindrical shoulder 47 having integral therewith and extending therefrom a reduced threaded portion 49 having integral therewith and extending there from a pointer 51 terminating in a needle point 53, two thrust washers 55 and a cylindrical nut 57 with knurling 59 formed thereon to facilitate manipulation thereof. Reduced cylindrical shoulder 47 is complemental to the hole of thrust washer 55.

As viewed in FIG. 2, flat body 29 has three, similarly configured, elongated and parallel slots 61, 63 and 65, each of whose dimensional widths is of the same dimensional size as the diameter of reduced shoulder 47. The dimensional width of each of the intermediate horizontal portions 33 and 35 is twice the dimensional width of the top and bottom horizontal portions 31 and 37.

Each of the thrust washers 55 represents an annulus whose radial ring dimension 67 is the difference between the exterior radius of washer 55 less the radius of the washer hole. Such radial ring dimension 67 is less than the dimensional width of either the top or bottom horizontal portions 31 or 37, thereby permitting any three markers 43 to be disposed in aligned vertical relationship on each of the slots 61, 63 and 65, as will be discerned from the description and explanation of the assembly and securement of the markers 43 with reference to the slots 61, 63 or 65, and such that none of the thrust washers 55 in such vertically aligned disposition will interfere with one another.

In such assembly and securement of one of the markers 43 with reference to one of the slots 61, 63 or 65, one of the washers 55 is appropriately disposed on reduced cylindrical shoulder 47, then shoulder 47 is appropriately disposed through such slot (either 61, 63 or 65), then the second washer 55 is appropriately disposed on reduced shoulder 47, and then cylindrical nut 57 is threadingly engaged with threaded portion 49 and appropriately tightened. If such marker 43, for example, is disposed with reference to slot 61, then the thrust washers 55 will be disposed in abutting and engaging securement with top horizontal portion 31 and intermediate horizontal portion 33.

The analytical instrument 25 is shown in FIG. 2 as being in alignment with the profile diagram 1 in FIG. 1 such that the aligned left vertical edges 69, 71 and 73 of their respective slots 61, 63 and 65 are in corresponding alignment with vertical line 5 of profile diagram 1, and the needle pointers 53 of the markers 43 are in corresponding alignment with the peak points 11, 13, 15, 17, 19, 21 and 23. Such foregoing described alignments would be demonstrated were discrete imaginary lines drawn vertically from FIG. 1 to FIG. 2. Similarly, in operative utilization of the analytical instrument 25, the exterior edge of left vertical side 39 could be disposed in alignment with vertical line 5 of profile diagram 1, or, similarly, one of the markers 43 could be appropriately disposed on and to the left-side portion of analytical instrument 25 such that its cooperating associated needle point 53 will be placed upon vertical line 5.

Such peak points 11, 13 and 15 are shown relatively close to one another. From the foregoing description it should be discerned and appreciated that the analytical instrument 25 possesses the phenomenon of adjustability of its markers 43 such that any three markers 43 can be disposed in absolutely aligned vertical relationship on each of the slots 61, 63 and 65, and such that none of the thrust washers 55 of such absolutely aligned and vertically disposed markers will physically interfere with one another.

Hence, from the description and explanation of the assembly and securement of the markers 43 with reference to the slots 61, 63 and 65, it should be appreciated that the markers 43 are adjustable in a horizontal direction relative to and coaxial with the longitudinal axes of such parallel slots 61, 63 and 65, and that the analytical instrument 25 has the phenomenon of adjustability and disposition of its markers 43 such that any three markers 43 constituting its own set can be disposed, each relative to its own slot, in absolutely aligned vertical relationship normal to the longitudinal axes of such parallel slots 61, 63, and 65.

The analytical instrument 25 of this invention can be similarly utilized in connection with any identifying profiles of any materials that exhibit or that can be caused to exhibit such identifying profiles, such as by means of chromatograms, spectroscopic profiles, optical laser spectra or magnetic spectra or combinations thereof or by means of any other detection systems exhibiting identifying profiles.

As has been mentioned and described with respect to gas chromatography, discrete components emerge or elute after corresponding discrete retention times with the rise or fall of their peaks indicating the concentrations of such components.

The analytical instrument 25 of this invention can be utilized to monitor the gas chromatograph to determine whether such equipment is working properly. In this connection, prior chromatograms of known samples of the properly functioning gas chromatograph are utilized. The markers 43 of the analytical instrument 25 are disposed such that their needle points 53 are placed upon the points on the X axis of the chromatogram resulting from vertical lines drawn from the peaks of such known samples to such X axis. Hence, such analytical instrument 25 with such pre-set markers 43 can be utilized to determine whether the gas chromatograph is functioning properly by simply ascertaining whether the needle points 53 of such pre-set markers 43 line up with the peaks of such known samples profiled upon the new chromatogram of the chromatograph being operated.

The elongated cylindrical bodies 45 of the markers 43 are of different colors in order that color-coding may be resorted to when utilizing the analytical instrument 25 and utilizing such colored markers 43 as reference markers. For example, the analytical instrument 25 can be utilized when a municipal water supply is being hourly or routinely monitored for contaminants. In this application, the known components are pin-pointed and localized with pre-set markers 43, each of whose cylindrical bodies is of a certain but different color. In this described application of the analytical instrument 25, it is a relatively simple matter to immediately detect on the most recent chromatogram any unknown component or contaminant being eluted from the chromatograph's column for reason of the fact that any such unknown component or contaminant profiled on such most recent chromatogram will lack a pre-set pin-pointing marker 43 because such unknown component or contaminant will have a retention time for its elution that is different from the discrete retention times of their respective known components.

INDUSTRIAL APPLICABILITY

As should now be obvious from the description and nature of the analytical instrument 25 of this invention, same can be utilized and exploited by industries and laboratories employing detection systems to exhibit identifying profiles of materials, and same can be utilized and exploited by schools and colleges teaching the use and interpretation of detection systems and the identifying profiles which such detection systems exhibit, for the purposes set forth hereinbefore, to wit: to monitor and determine easily, quickly and immediately whether such detection systems and equipment are working properly, and to localize known components profiled to easily, quickly and immediately detect in routine monitoring of materials any unknown component profiled or being profiled by such detection equipment.

What is claimed is:

1. An analytical instrument for use with profile diagrams of materials exhibited by a detection system to monitor, detect and determine whether such detection system is working properly, and to detect in the monitoring of materials any unknown component profiled by such detection system, said analytical instrument comprising: a body means, slot means for receiving markers for securement therewith and markers; said markers having means cooperating with said slot means to permit adjustable disposition and securement where disposed of said markers relative to said slot means, said markers thusly being adjustably disposable and securable respecting said slot means to pin-point discrete points of known samples of components of materials profiled by such profile diagram to thereby serve as pin-pointing reference markers for such known components for monitoring, detecting and determining whether such detection system is working properly, and to detect in such monitoring of materials any unknown component profiled by such detection system by such unknown component lacking a pin-pointing reference marker.

2. An analytical instrument of claim 1 wherein said body means comprises a flat, rectangular-shaped body.

3. An analytical instrument of claim 1 wherein said body means has top, intermediate and bottom horizontal portions, and left and right vertical sides, forming thereby said slot means.

4. An analytical instrument of claim 1 wherein said body means comprises a flat, rectangular-shaped body and wherein said body means has top, intermediate and bottom horizontal portions, and left and right certical sides, forming thereby said slot means.

5. An analytical instrument of claim 4 wherein said horizontal portions are in parallel relationship with one another and said vertical sides are in normal relationship to said horizontal portions.

6. An analytical instrument of claim 1 wherein said body means comprises a flat, rectangular-shaped body having top, intermediate and bottom horizontal portions, and left and right vertical sides, forming thereby said slot means, wherein said horizontal portions are in parallel relationship with one another and said vertical sides are in normal relationship to said horizontal portions, and wherein said slot means comprises elongated and parallel slots.

7. An analytical instrument of claim 1 wherein said markers terminate in needle points and wherein said needle points serve as such pin-pointing reference markers to pin-point such discrete points of such known components.

8. An analytical instrument of claim 1 wherein said means of said markers cooperating with said slot means comprises washers, shoulders, threaded portions and nuts, wherein said slot means receives said shoulders, wherein said shoulders carry said washers for abutting and engaging securement with said body means and wherein said nuts threadingly engage said threaded portions.

9. An analytical instrument of claim 1 wherein said markers terminate in needle points serving as such pin-pointing reference markers to pin-point such discrete points of such known components, wherein said means of said markers cooperating with said slot means comprises washers, shoulders, threaded portions and nuts, wherein said slot means comprises elongated and parallel slots, wherein said slots receive said shoulders, wherein said body means has horizontal portions, wherein said shoulders carry said washers for abutting and engaging securement with said horizontal portions and wherein said nuts threadingly engage said threaded portions.

10. An analytical instrument of claim 9 wherein said body means comprises a flat, rectangular-shaped body having said horizontal portions in parallel relationship with one another, and laft and right vertical sides, forming thereby said elongated and parallel slots, wherein said vertical sides are in normal relationship to said horizontal portions, wherein said parallel slots have longitudinal axes, wherein said slots permit said markers to be adjustably disposed and secured in a horizontal direction relative to and coaxial with said longitudinal axes of said slots and wherein said markers can be disposed, each relative to its own slot, in aligned vertical relationship normal to said longitudinal axes of said parallel slots.

* * * * *